(12) United States Patent
Guo et al.

(10) Patent No.: US 6,689,817 B1
(45) Date of Patent: Feb. 10, 2004

(54) PROCESS FOR PREPARING GUAIFENESIN TANNATE

(75) Inventors: Cheng Guo, Parsippany, NJ (US); Vilas M. Chopdekar, Edison, NJ (US)

(73) Assignee: Jame Fine Chemicals, Inc., Bound Brook, NJ (US)

( * ) Notice: Subject to any disclaimer, the term of this patent is extended or adjusted under 35 U.S.C. 154(b) by 23 days.

(21) Appl. No.: 10/017,137

(22) Filed: Dec. 14, 2001

(51) Int. Cl.[7] .................. A61K 31/075; A61K 31/70; A61K 9/20; C07C 69/88; C07C 41/00
(52) U.S. Cl. .................. 514/718; 424/464; 514/23; 560/68; 568/648
(58) Field of Search .................. 424/464; 514/23, 514/718; 560/68; 568/648

(56) References Cited

U.S. PATENT DOCUMENTS

| 5,599,846 | A | | 2/1997 | Chopdekar et al. | ......... 514/653 |
| 5,663,415 | A | * | 9/1997 | Chopdekar et al. | ........... 560/68 |
| 6,037,358 | A | | 3/2000 | Gordziel | ...................... 514/357 |
| 6,287,597 | B1 | | 9/2001 | Gordziel | ...................... 424/464 |
| 6,306,904 | B1 | | 10/2001 | Gordziel | ...................... 514/530 |

* cited by examiner

Primary Examiner—Alan L. Rotman
Assistant Examiner—Taylor V Oh
(74) Attorney, Agent, or Firm—Jack Matalon

(57) ABSTRACT

The invention pertains to a process for preparing guaifenesin tannate. The process involves the steps of mixing guaifenesin with tannic acid in the presence of water, continuing to mix the reaction mixture for about 5 minutes to about 4 hours and thereafter removing at least about 80 wt.% of the water by freeze-drying the reaction mixture.

8 Claims, No Drawings

PROCESS FOR PREPARING GUAIFENESIN TANNATE

FIELD OF THE INVENTION

The invention pertains to a process for preparing guaifenesin tannate.

BACKGROUND OF THE INVENTION

Guaifenesin is a well-known commercially available compound. It is frequently referred to as guaiphenesin or glyceryl guiacolate. Its chemical name is 3-(2-methoxyphenoxy)-1,2-propanediol. It is a solid having a melting point of 78.5° C, and its molecular formula is $C_{10}H_{14}O_4$. It is only slightly soluble (i.e, about 5 wt. %) in water, but is readily soluble in alcohols such as methanol, ethanol, isopropanol, etc. By way of further identification, its CAS number is 93-14-1.

Guaifenesin finds its principal use as an expectorant for promoting or facilitating the removal of secretions from the respiratory tract in a warm-blooded animal, principally a human being. It helps to loosen phlegm (mucus) and thin bronchial secretions to rid the bronchial passageways of bothersome mucus, drain bronchial tubes and makes coughs more productive. It is typically administered to human beings in need of such medication in the form of tablets and/or suspensions.

Guaifenesin has also proven useful as a central nervous system muscle relaxant for non-human warm-blooded animals, particularly horses and cattle. For animals in need of a muscle relaxant, guaifenesin is typically administered in injectable form.

In recent years, research has indicated that guaifenesin may be useful for alleviation of the symptoms of fibromyalgia syndrome and chronic fatigue syndrome. If such research proves that guaifenesin does in fact alleviate the symptoms of FMS and CFS, it will be a very welcome adjunct in the treatment of these syndromes which are quite painful.

In contradistinction to the antihistamines of which many are unstable in the form of their free bases, guaifenesin is relatively stable. Therefore, little, if any attention, has been paid in recent years to improving guaifenesin compositions. On the other hand, there is a considerable amount of prior art which has emerged in recent years which has been directed to salts of antihistamines, principally tannate salts, which stabilize the antihistamine bases. For example, see U.S. Patents 5,599,846; 5,663,415; 6,037,358; 6,287,597; and 6,306,904.

Tannic acid is commercially available and is used in many industrial applications. It is frequently referred to as gallotannic acid, gallotannin; glycerite or tannin. It is a pale tan powder having a decomposition point of 210–215° C., and is highly soluble in water and alcohols. Its molecular formula is $C_{76}H_{52}O_{46}$ and its CAS number is 1401-55-4. Tannic acid is typically produced from Turkish or Chinese nutgall and has a complex non-uniform chemistry and typically contains about 5–10 wt. % water.

As mentioned above, guaifenesin, in contradistinction to the antihistamines, is quite stable and therefore would not require the addition of a material such as tannic acid to render it stable. However, guaifenesin does have one drawback: it is readily absorbed in the patient's body, but its action is relatively short-lived. Indeed, its plasma half-life is only one hour. Accordingly, while it provides relatively quick relief to the patient, the patient is required to take relatively high doses several times a day until the condition which necessitated the administration of the guaifenesin has been alleviated. This presents a particular problem to the patient suffering from chronic bronchitis who is therefore required to be on a constant regimen of guaifenesin, thereby increasing the likelihood of the occurrence of undesirable side effects.

It would be very desirable if a form of guaifenesin was available which would have extended-release properties, i.e., the guaifenesin would be slowly released into the patient's bloodstream over a prolonged period of time. Thus far, the only slow-release forms of guaifenesin which are available are those such as polymer coated tablets. Such prior art formulations provide mixed results in that the guaifenesin is not available for adsorption into the patient's bloodstream until the polymeric coating has been dissolved, but thereafter the guaifenesin is quickly absorbed and metabolized. The result is that frequently, the guaifenesin must again be administered to the patient within the period of only a few hours.

Commercially available antihistamine tannate compositions are relatively impure. Such compositions are typically prepared by reacting the antihistamine free base with tannic acid in the presence of a volatile solvent, usually isopropanol. The yield is only fair (e.g. about 70%) and decomposition products e.g. 2–5 wt. %, and a significant amount of the volatile solvent, e.g. 6–10 wt. %, based on the weight of the composition, remains with the product and cannot be removed.

U.S. Patent 5,663,415 discloses a process for preparing antihistamine tannates which involves the reaction between the antihistamine free base and tannic acid in aqueous media to form an aqueous solution of the antihistamine tannate. Since the resultant antihistamine tannate is generally heat sensitive, the antihistamine tannate is recovered from the aqueous solution by freeze-drying. The process disclosed in the '415 patent results in a pure product in which the only residual impurity is water in the amount of less than 10 wt. %

However, guaifenesin is not an antihistamine and accordingly it does not contain a nitrogen atom which would result in a reaction to produce a tannate salt. Guaifenesin is a diol and it would have been expected that it could react with tannic acid to form a new composition. It has been surprisingly found that guaifenesin tannate can be prepared by the process of the present invention and that the guaifenesin tannate is not a salt, but rather is believed to be a complex.

DETAILED DESCRIPTION OF THE INVENTION

It has now been found that it is possible to provide an extended-release form of guaifenesin by reacting it with tannic acid to form a composition hereinafter referred to as guaifenesin tannate.

The guaifenesin tannate is prepared by a method involving the following steps:

(a) mixing guaifenesin with tannic acid in the presence of water;

(b) continuing to mix the reaction mixture resulting from step (a) for a period of time of about 5 minutes to about 4 hours; and (c) freeze-drying the reaction mixture resulting from step (b) at a temperature and at a reduced pressure for such period of time that at least about 80 wt. % of the water is removed from the reaction mixture.

Steps (a) and (b) may be effected by any type of desired mixing, such as conventional stirrers. To insure that as much guaifenesin tannate product as possible is recovered, it is preferred that the entire mass of reaction mixture resulting from step (b) be subjected to freeze-drying.

Typically, the guaifenesin will be present in the amount of about 1 to about 5, preferably 1 to 4, moles of guaifenesin per mole of tannic acid. The amount of water utilized in step (a) is not critical. Preferably, the water is present in an amount such that the weight ratio of tannic acid to water is in the range of 1:10 to 10:1. Preferably, the mixing time in step (b) is 15 minutes to 2 hours.. The temperature at which steps (a) and (b) are carried out are not critical and may vary from about 20 to about 80° C. After step (b) has been completed, the reaction mass is cooled to room temperature.

The water is removed from the reaction mixture by freeze drying. Although freeze-drying to remove the water is a time-consuming process (a reaction mixture containing 1 liter of water will typically take 30–36 hours to remove about 97 wt. % of the water present in the reaction mixture), it has been found to be the only method for removing water from the guaifenesin tannate without any significant formation of decomposition products.

The freeze-drying of the reaction mixture resulting from step (b) will typically be carried out at a reduced pressure and reduced temperature, e.g. a pressure of not greater than about 500 milliTorr, preferably 300 to 100 milliTorr and at a temperature in the range of about –60° C. to –20° C., preferably -50° to 40° C. The desired end point of the freeze-drying process may be determined by condensing and measuring the quantity of water vapor removed during the freeze-drying process. Preferably, the freeze-drying operation is conducted such that at least about 90 wt. % of the water is removed from the reaction mixture. The time required for completion of the freeze-drying process will vary depending on factors such as pressure, temperature, quantity to be freeze-dried, desired level of water to be tolerated in the final product, the thickness and surface area of the reaction mixture layers in the trays of the freeze-drying equipment, etc. After the freeze-drying has been completed, the guaifenesin tannate may be milled into a fine powder typically having a particle size of about 50 to about 200 mesh.

It has been found that process of the invention results in the production of pure guaifenesin tannate compositions having a minimum purity level of at least 90 wt. %, usually at least 95 wt. % and often at least 98 wt. %, based on the weight of the composition, with a yield of at least about 90% and often with a yield in excess of 97%. The chief "impurity" present in the guaifenesin tannate prepared by the process of the invention is water which is present in an amount of about 1 to about 10 wt. %, based on the weight of the composition. Indeed, it has been found possible to produce guaifenesin tannate compositions having a purity level of at least 99 wt % and a water content of less than 1 wt. %, based on the weight of the composition.

Since the pure guaifenesin tannate compositions prepared by the process of the invention are administered either in solid form, eg., a pill, or as a suspension, e.g., a syrup, the minimal amount of water present in the composition cannot be considered to be an impurity of the nature associated with degradation products or volatile organic compounds such as isopropanol. The dosage to be administered can be readily adjusted by taking into account the insignificant amount of water present in the composition.

The guaifenesin tannate produced by the process of the invention has a softening point in the range of 57 to 62° C. when freeze-dried to a moisture content of less than about3 wt. % (as determined by Karl Fischer analysis); of course, the softening point will be lower for guaifenesin tannate compositions containing higher amounts of moisture. By contrast, guaifenesin has a melting point of 78.5° C. and tannic acid decomposes at 210–215°C.

The guaifenesin tannate produced by the process of the invention is a light tan-colored powder which is soluble in water and alcohols, but is insoluble in methylene chloride, chloroform or toluene. In contradistinction thereto, guaifenesin is a white powder which is soluble in water, alcohols and methylene chloride and sparingly soluble in toluene, while tannic acid is a tan-colored powder which is soluble in water and alcohols, but is insoluble in methylene chloride, chloroform or toluene. Further proof that the guaifenesin tannate produced by the process of the present invention is a new material and not a physical mixture of guaifenesin and tannic acid has been obtained by the use of FTIR spectroscopy which is discussed below.

It would have been expected that the guaifenesin tannate resulting from the two step method described above would have the structure of an ester since the reaction involves an alcohol, i.e., guaifenesin which is a diol, and an acid, i.e., tannic acid. It is well known that in the course of a typical esterification reaction, water is formed as a by-product. However, it was found that the reaction between the guaifenesin and the tannic acid in accordance with the process of the invention takes place in the presence of, and is facilitated by, water. Accordingly, it is believed that the guaifenesin tannate is a complex.

The guaifenesin tannate produced by the process of the invention may be prepared for oral administration in the form of powders, capsules, elixirs, syrups, etc. Preferably the compositions are prepared in the form of tablets containing about 100 to about 500 mg of guaifenesin tannate per tablet or as a suspension, ie., liquid, wherein each 5 ml (teaspoon) of liquid would contain about 100 to about 400 mg of guaifenesin tannate..

Tablets containing the guaifenesin tannate produced by the process of the invention may be prepared in a conventional manner by the addition of suitable pharmaceutical carriers, including fillers, diluents, lubricants and the like as well as conventional and well known binding and disintegrating agents. A typical tablet composition of the present invention will contain, in addition to the guaifenesin tannate, microcrystalline cellulose, corn starch, magnesium stearate, croscarmellose sodium and coloring matter.

The suspension formulations of the guaifenesin tannate produced by the process of the present invention will typically additionally contain citric acid, caramel, glycerin, sorbitol solution, propylene glycol, saccharin sodium, sodium benzoate, flavoring agent and purified water.

When intended for use as a muscle relaxant for non-human animals such as horses and cattle, the guaifenesin tannate produced by the process of the invention will be administered in injectable form containing about 50 to about 200 mg per ml of the guaifenesin tannate. Each ml of the injectable liquid typically would additionally contain about 25 to 100 mg dextrose (anhydrous), about 10 to about 40 mg propylene glycol, about 5 to about 20 mg of dimethylacetamide (parental grade), about 0.25 to 1 g of edetate disodium and water for injection q.s.

If desired, the guaifenesin tannate produced by the process of the invention may be formulated with other pharmaceutically active ingredients such as antihistamines and antitussives, e.g., chlorpheniramine, brompheniramine, pyrilamine, phenylephrine, ephedrine, pseudoephedrine, dextromethorphan, carbetapentane, carbinoxamine, and the like. Typically, these other active ingredients will be employed in the form of their free bases or their salts, e.g., citrates, maleates, hydrobromides, hydrochlorides, tannates, etc.

Of course, the dosage of the guaifenesin tannate prepared by the process of the invention, alone or in combination with other pharmaceutically active ingredients to be administered, will be dependent on the age, health and weight of the recipient, types of concurrent treatment, if any, frequency of treatment and effect desired.

The following nonlimiting examples will serve to illustrate the present invention.

EXAMPLE 1

Guaifenesin tannate was prepared as follows. In a 1-liter beaker were placed 340 g tannic acid (0.2 m), 163 g water and 39.6 g (0.2 m) of guaifenesin. The mixture was heated to a temperature of 35–50° C. and was stirred for 1 hour. After cooling to room temperature, the entire reaction mixture was freeze dried at a reduced pressure of 200–100 milliTorr and a temperature of −50 to −40° C. for about 36 hours. At this point, the water which had been removed was condensed and its weight equaled about 160 g. The yield of guaifenesin tannate was 365 g (96.15% of theory).

EXAMPLE 2

Example 1 was repeated using a guaifenesin: tannic acid molar ratio of 2: 1. In a 1-liter beaker were placed 340 g tannic acid (0.2 m), 180 g water and 79.3 g (0.4 m) of guaifenesin. The mixture was heated to a temperature of 35–50° C. and was stirred for 1 hour. After cooling to room temperature, the entire reaction mixture was freeze dried at a reduced pressure of 200–100 milliTorr and a temperature of −50 to −40° C. for about 36 hours. At this point the water which had been removed was condensed and its weight equaled about 176 g. The yield of guaifenesin tannate was 405 g (96.6% of theory).

EXAMPLE 3

Example 1 was repeated using a guaifenesin: tannic acid molar ratio of 5: 1. In a 1-liter beaker were placed 340 g tannic acid (0.2 m), 230 g water and 198.2 g (1 m) of guaifenesin. The mixture was heated to a temperature of 35–50° C. and was stirred for 1 hour. After cooling to room temperature, the entire reaction mixture was freeze dried at a reduced pressure of 200–100 milliTorr and a temperature of −50 to −40° C. for about 36 hours. At this point, the water which had been removed was condensed and its weight equaled about 220 g. The yield of guaifenesin tannate (which had a wet appearance) was 526 g (97.7% of theory).

EXAMPLE 4

Two gram samples of finely milled guaifenesin tannate powders were taken from each of the products prepared in Examples 1–3. Each sample was mixed with 110 g of methylene chloride and was stirred for 10 minutes at ambient temperature. Each mixture was then filtered. The insoluble material was dried and weighed and the filtrate was evaporated to dryness and the residue was weighed The results were as follows:

| Example | Insoluble Ppt., g | Soluble Ppt., mg |
| --- | --- | --- |
| 1 | 1.94 | <8 |
| 2 | 1.95 | <10 |
| 3 | 1.945 | <7 |

The results set forth above indicate that the guaifenesin tannate prepared by the process of the invention is insoluble in methylene chloride and only an insignificant fraction of the product was soluble in methylene chloride ( the soluble fraction appears to be unreacted guaifenesin). These results further indicate that the guaifenesin tannate is a complex of guaifenesin and tannic acid..

Analysis of the guaifenesin tannate by FTIR spectroscopy showed the following: no peaks present at 2350 $cm^{-1}$, moderately-sized sharp peaks at 1700 and 1600 $cm^{-1}$, a large sharp peak at 1500 $cm^{-1}$, moderately-sized sharp peaks at 1425 and 1325 $cm^{-1}$, a large sharp peak at 1025 $cm^{-1}$ and a very large sharp peak at 745 $cm^{-1}$.

By way of contrast, analysis of tannic acid by FTIR spectroscopy showed the following peaks: a short, broad peak extending from 3400 to 3100 $cm^{-1}$, a moderately-sized sharp peak at 2350 $cm^{-1}$, moderately-sized sharp peaks at 1700 and 1600 $cm^{-1}$, no peak at 1500 $cm^{-1}$, a very large sharp peak at 1175 $cm^{-1}$, a large sharp peak at 1025 $cm^{-1}$ and a moderately-sized peak at 750 $cm^{-1}$.

Analysis of guaifenesin by FTIR spectroscopy showed the following peaks: a small-sized peak at 3250 $cm^{-1}$, a very short peak at 2400 $cm^{-1}$, a small-sized peak at 1600 $cm^{-1}$, a large sharp peak at 1500 $cm^{-1}$, a moderately-sized sharp peak at 1450 $cm^{-1}$, short, sharp peaks at 1400, 1350 and 1300 $cm^{-1}$, large-sized, sharp peaks at 1250 and 1200 $cm^{-1}$, a short, sharp peak at 1175 $cm^{-1}$, large-sized sharp peaks at 1100 and 1075 $cm^{-1}$, large-sized sharp peaks at 1050, 1025 and 1000 $cm^{-1}$, moderate-sized peaks at 950, 900 and 850 $cm^{-1}$, a large-sized sharp peak at 775 $cm^{-1}$ and a very large-sized sharp peak at 750 $cm^{-1}$.

What is claimed is:

1. A process for preparing guaifenesin tannate which comprises the steps of:

(a) mixing guaifenesin with tannic acid in the presence of water;

(b) continuing to mix the reaction mixture resulting from step (a) for a period of time of about 5 minutes to about 4 hours; and (c) freeze-drying the reaction mixture resulting from step (b) at a temperature of about −60° C. to −20° C. and at a reduced pressure of not greater than about 500 milliTorr for such period of time that at least about 80 wt. % of the water is removed from the reaction mixture.

2. The process of claim 1 wherein the guaifenesin is present in the amount of about 1 to about 5 moles of guaifenesin per mole of tannic acid.

3. The process of claim 2 wherein the guaifenesin is present in the amount of 1 to 4 moles of guaifenesin per mole of tannic acid.

4. The process of claim 1 wherein the water is present in an amount such that the weight ratio of tannic acid to water is in the range of 1:10 to 10:1.

5. The process of claim 1 wherein the mixing time in step (b) is in the range of 15 minutes to 2 hours.

6. The process of claim 1 wherein the freeze-drying is carried out at a pressure in the range of 300 to 100 milliTorr and a temperature in the range of −50 to −40° C.

7.The process of claim 1 wherein steps (a) and (b) are carried out at temperature in the range of about 20 to about 100° C.

8. The process of claim 1 wherein the freeze-drying in step (c) is carried out for a period of time such that at least about 90 wt. % water is removed from the reaction mixture.

* * * * *